United States Patent
Kim et al.

(10) Patent No.: US 11,135,028 B2
(45) Date of Patent: Oct. 5, 2021

(54) SOFT SURGICAL TOOLS

(71) Applicant: CHILDREN'S NATIONAL MEDICAL CENTER, Washington, DC (US)

(72) Inventors: Peter C. Kim, Washington, DC (US); Justin D. Opfermann, Washington, DC (US); Axel Krieger, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 100 days.

(21) Appl. No.: 15/771,689

(22) PCT Filed: Oct. 31, 2016

(86) PCT No.: PCT/US2016/059753
§ 371 (c)(1),
(2) Date: Apr. 27, 2018

(87) PCT Pub. No.: WO2017/075602
PCT Pub. Date: May 4, 2017

(65) Prior Publication Data
US 2018/0338807 A1 Nov. 29, 2018

Related U.S. Application Data

(60) Provisional application No. 62/249,195, filed on Oct. 31, 2015.

(51) Int. Cl.
*A61B 34/37* (2016.01)
*B25J 9/14* (2006.01)
(Continued)

(52) U.S. Cl.
CPC .......... *A61B 34/37* (2016.02); *A61B 17/0218* (2013.01); *A61B 17/28* (2013.01);
(Continued)

(58) Field of Classification Search
CPC ......... A61B 90/60; A61B 34/25; A61B 34/37; B25J 9/142; B25J 15/10
See application file for complete search history.

(56) References Cited

U.S. PATENT DOCUMENTS 8,034,065 B2* 10/2011 Coe ........................ A61F 5/0053
606/157
2008/0064921 A1* 3/2008 Larkin ..................... A61B 1/05
600/104
(Continued)

FOREIGN PATENT DOCUMENTS

JP 9-98978 4/1997
JP 2000-5189 A 1/2000
(Continued)

OTHER PUBLICATIONS

International Search Report and Written Opinion dated Jan. 9, 2017, in PCT/US2016/059753 filed Oct. 31, 2016.
(Continued)

*Primary Examiner* — Thomas McEvoy
(74) *Attorney, Agent, or Firm* — Oblon, McClelland, Maier & Neustadt, L.L.P.

(57) ABSTRACT

A method is provided for making an appendage of a soft surgical tool, including: receiving a set of mechanical constraints for a surgical procedure; calculating a set of articulation states based on the set of mechanical constraints; generating a plurality of print commands for printing an appendage configured to form the set of articulation states based on the calculation; and printing an appendage based
(Continued)

on the plurality of print commands. Multiple printed appendages can be formed into an orienting assembly.

12 Claims, 13 Drawing Sheets

(51) Int. Cl.
*B25J 15/10* (2006.01)
*B25J 15/12* (2006.01)
*A61B 17/02* (2006.01)
*A61B 17/28* (2006.01)
*A61B 34/00* (2016.01)
*A61B 90/00* (2016.01)
*A61B 17/29* (2006.01)
*A61B 17/32* (2006.01)
*A61B 17/00* (2006.01)
*A61B 1/313* (2006.01)

(52) U.S. Cl.
CPC ............. *A61B 17/29* (2013.01); *A61B 34/25* (2016.02); *A61B 90/06* (2016.02); *B25J 9/142* (2013.01); *B25J 15/10* (2013.01); *B25J 15/12* (2013.01); *A61B 1/3132* (2013.01); *A61B 17/320016* (2013.01); *A61B 34/76* (2016.02); *A61B 90/361* (2016.02); *A61B 2017/00022* (2013.01); *A61B 2017/00477* (2013.01); *A61B 2017/00526* (2013.01); *A61B 2017/00557* (2013.01); *A61B 2017/0225* (2013.01); *A61B 2017/2937* (2013.01); *A61B 2090/065* (2016.02)

(56) References Cited

U.S. PATENT DOCUMENTS

2014/0109560 A1    4/2014  Ilievski et al.
2014/0318118 A1*  10/2014  Mazzeo ................... F03G 7/06
                                                                60/527
2015/0257839 A1*   9/2015  Vause .............. A61B 17/22032
                                                               606/130
2015/0283699 A1*  10/2015  Morin .................... B25J 9/1075
                                                               700/259

FOREIGN PATENT DOCUMENTS

JP       2003-184818        7/2003
JP       2008-536552        9/2008
JP       2015-512795 A      4/2015
WO    WO 2012/484472 A2    11/2012
WO    WO 2013/146340 A2    10/2013
WO    WO 2014/196928 A1    12/2014
WO    WO 2014/201563 A1    12/2014
WO    WO 2015/047573 A1     4/2015
WO    WO 2015/102723 A2     7/2015
WO    WO 2015/157621 A1    10/2015

OTHER PUBLICATIONS

Extended European Search Report dated Aug. 28, 2019 in Patent Application No. 16861050.9.
Partial European Search Report dated May 22, 2019 in Patent Application No. 16861050.9, 17 pages.
Chinese Office Action dated Nov. 5, 2019 in Chinese Patent Application No. 201680072928.8, 1 page.
Combined Chinese Office Action and Search Report dated Mar. 4, 2020, in Patent Application No. 201680072928.8 (with English translation), 14 pages.
European Office Action dated Dec. 9, 2020 in corresponding European Patent Application No. 16 861 050.9 (5 pages).
Japanese Office Action (Notice of Reasons for Refusal) dated Oct. 20, 2020 in counterpart Japanese Patent Application No. 2018-522550 (11 pages).
Foreign Office Action issued in corresponding Chinese Application No. 201680072928.8, dated Jan. 7, 2021 (with machine translation, 28 pages).

* cited by examiner

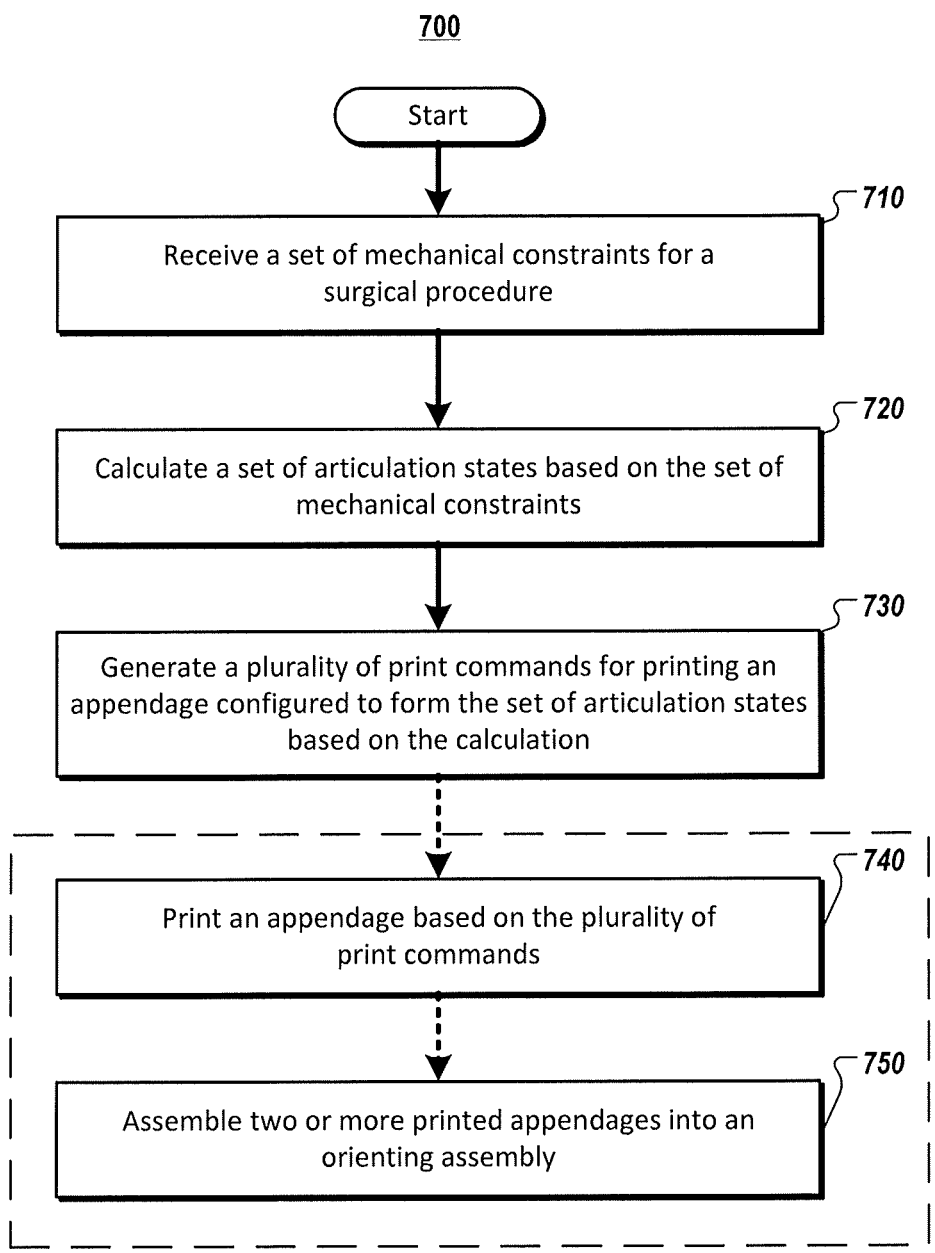

SOFT SURGICAL TOOLS

CROSS REFERENCES TO RELATED APPLICATIONS

This application claims priority from U.S. Application No. 62/249,195, filed Oct. 31, 2015, the content of which is incorporated by reference in its entirety.

BACKGROUND

Mechanized surgical tools for open and minimally invasive robotic surgical procedures have been developed to aid a surgeon in performing a surgical procedure. However, as robotic tools replace tactile feedback historically relied upon by the surgeon, unconstrained movements with hard instruments may continue to perforate, tear and damage a patient's tissue during the procedure. There is a need for soft surgical tools that are dexterous for the surgeon and also safe for the patient.

SUMMARY

A method is provided for making an appendage of a soft surgical tool, including: receiving a set of mechanical constraints for a surgical procedure; calculating a set of articulation states based on the set of mechanical constraints; generating a plurality of print commands for printing an appendage configured to form the set of articulation states based on the calculation; and printing an appendage based on the plurality of print commands. Multiple printed appendages can be formed into an orienting assembly.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 7A is a flowchart showing a method for making a soft surgical tool according to an example;

DETAILED DESCRIPTION

Figure 1:
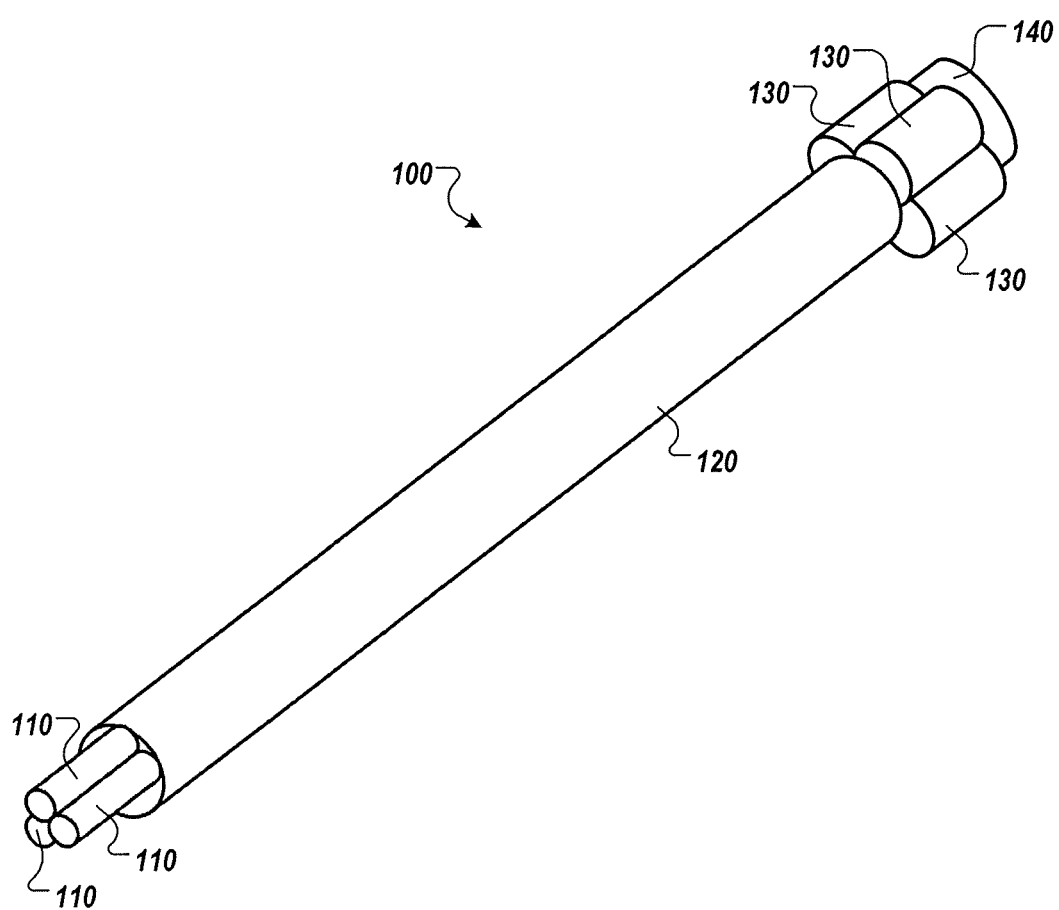
FIG. 1 is a perspective drawing of a soft surgical tool including a set of appendages, a sheath, a set of pumps, and a reservoir according to an example.

The present disclosure relates to a soft surgical tool and method of use in a surgical procedure. In particular, the disclosure describes the soft surgical tool having a set of soft appendages configured to selectively expose, retract, grasp, stabilize, and move tissues of interest. The soft surgical tool can be procedure specific as well as patient specific based on preoperative imaging. The soft surgical tool can include a sheath for housing the set of soft appendages and can be incorporated in a traditional hand tool for open surgical procedures, a minimally invasive tool for natural orifice, laparoscopic, arthroscopic, or other minimally invasive access, as well as a mechanized tool for open and minimally invasive robotic procedures.

Referring now to the drawings, wherein like reference numerals designate identical or corresponding parts throughout the several views.

FIG. 1 is a perspective drawing of a soft surgical tool 100 including a set of appendages 110, a sheath 120, a set of pumps 130, and a reservoir 140 according to an example. In an example, the soft surgical tool 100 can be inserted inside an abdominal cavity of a patient with the set of appendages 110 within the sheath 120. In an example, the sheath 120 can be retracted to expose the set of appendages 110. In another example, the set of appendages 110 can be actuated to extend beyond the sheath 120.

The set of appendages 110 can be actuated by pumping a gas/fluid into each appendage 100 to an actuated pressure. In an example, the gas is pressurized air or $CO_2$. In an example, the fluid is saline solution. In an aspect, the gas/fluid is preferred to be atraumatic to the tissue/patient such that when a leak occurs, the gas/fluid would not endanger the patient. In an example, each pump 130 can be connected to a respective appendage 110 by one or more inlets to control a direction and an amount of flow. (See FIG. 3A-3F)

Each appendage 110 can be made from a combination of a polymer configured to vary in stiffness such as silicone, as well as a blend of fibers and elastomers to create a variably-compliant actuated structure or a soft robotic actuator. Soft robotic actuators can be highly deformable to conform to arbitrary shapes and can be deployed in a tight space. In an example, each appendage 110 can be made from a polymer formed in a mold. In an aspect, the appendage 110 can be made from different parts and assembled into a final form. In an example, the appendage 110 can be made from a silicone material formed in a mold having the appendage shape which is then wrapped with a shape-memory material such as a Kevlar® thread (not shown). International patent application WO2015061444A1 titled "Soft robot device and related fabrication methods" describes a technique where a mold of a soft actuator can be designed and printed using additive manufacturing technologies.

In an example, each appendage 110 can be made from a 3D printed polymer. By varying a mechanical property of the polymer from rigid to compliant, each appendage 110 can be designed to follow preset trajectories when they are actuated. Additionally, materials used forming an appendage 110 are preferably both serializable and biocompatible. In a preferred embodiment, the soft surgical tool 100 is made from disposable components and intended for single use surgical applications. In an alternate embodiment, the soft surgical tool 100 can be covered in a thin film disposable sheath, so that it can be reused in more than one surgical procedure. In an alternative embodiment, the soft surgical tool 100 can be draped to keep the mechanical and non-sterilizable components isolated from the surgical field.

Articulation Shape and Articulation State

Figure 2A:
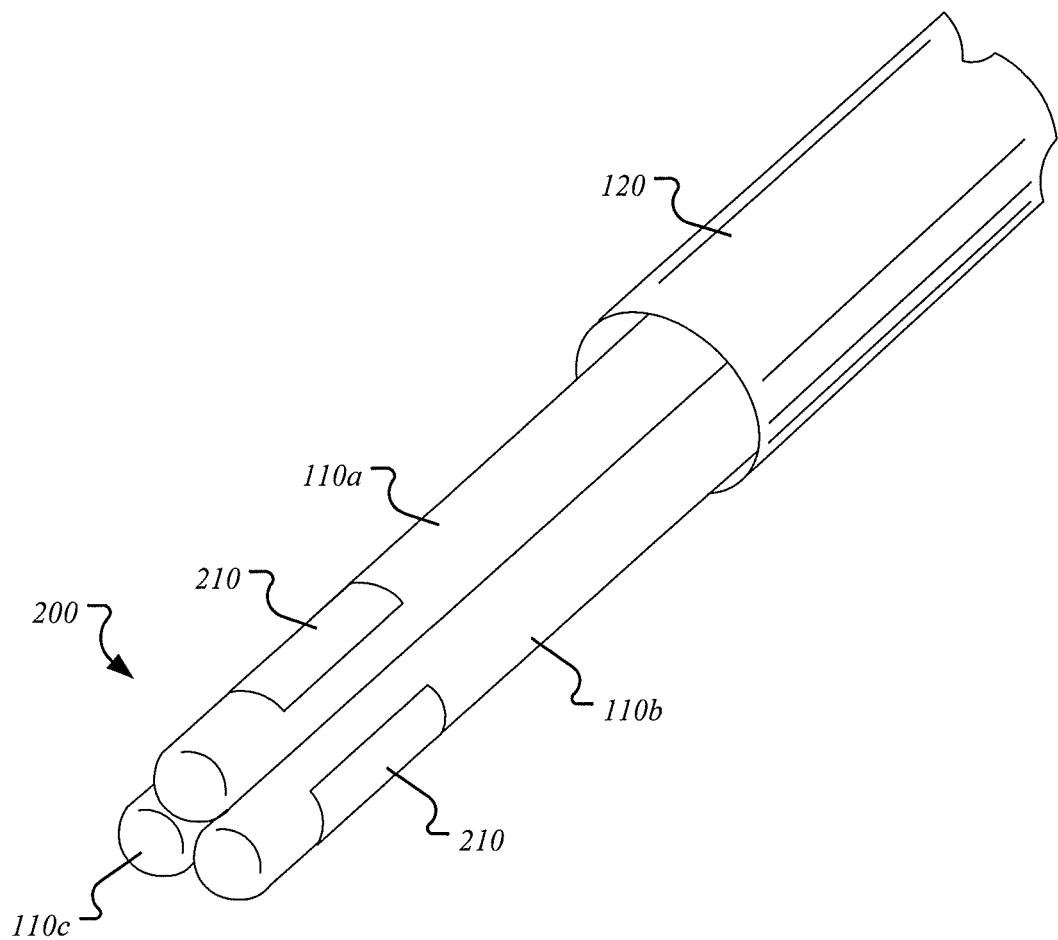
FIG. 2A is a perspective drawing of close up of a distal tip of the soft surgical tool illustrating each appendage including one or more sensors configured to contact and sense a tissue property according to an example.
Figure 2B:
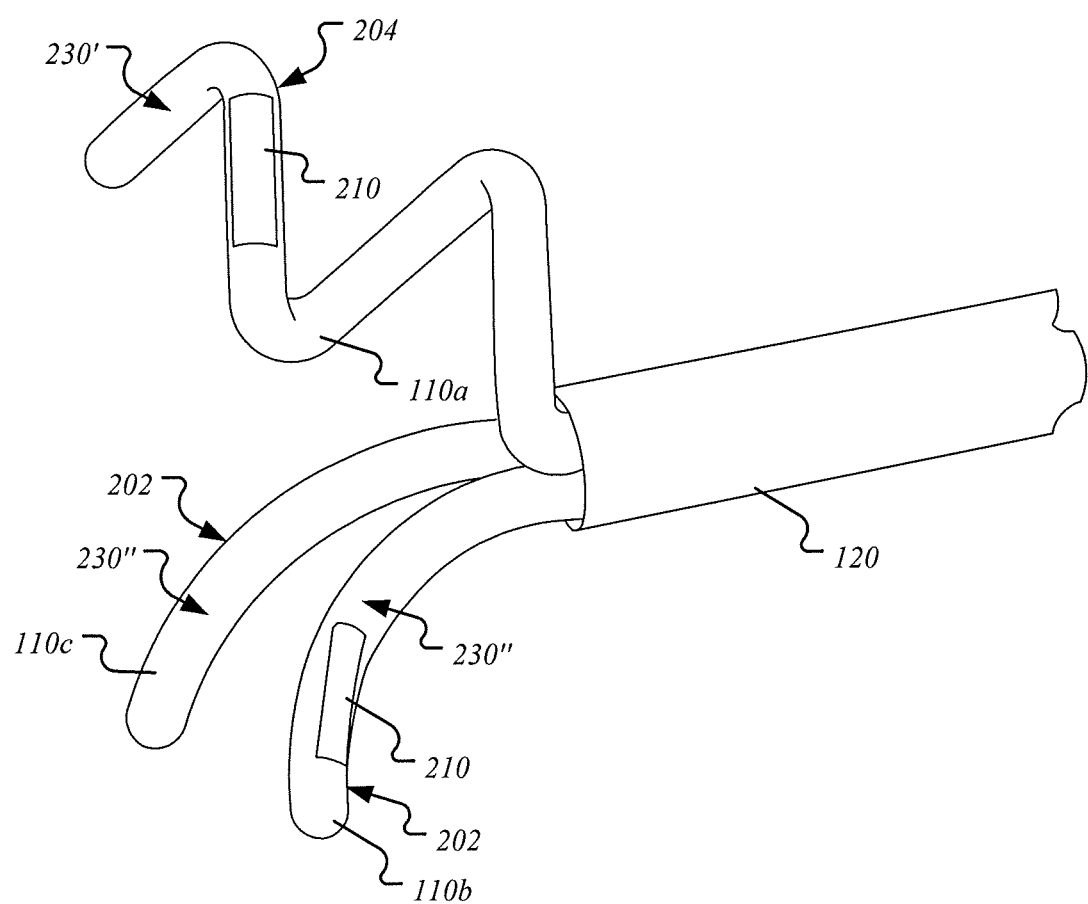
FIG. 2B is a perspective drawing of close up of a distal tip of the soft surgical tool illustrating each appendage actuated out of plane, including one appendage forming a helical structure according to an example.

FIG. 2A is a perspective drawing of close up of a distal tip of the soft surgical tool 100 illustrating each appendage 110a-c having an articulation shape 200 in-plane with the sheath 120. FIG. 2B is a perspective drawing of close up of a distal tip of the soft surgical tool 100 illustrating each appendage 110a-c actuated out of plane according to an example. The appendage 110a is shown forming an articulation shape 204 having a helical structure. The appendages 110b-110c each are actuated into an articulation shape 202 having a generally curved shape. In an example, the articulation shape 200 can be set by mechanically biasing an opposing compliant wall with a rigid wall of the appendage 110 (See FIGS. 3A-F). In an example, the rigid wall is relative to the compliant wall. For example, the rigid wall can be considered a relatively rigid wall as compared to the compliant wall. In an example, the articulation shape 200 can be set by modifying an amount of pressurized gas/fluid delivered to the appendage 110 by at least one pump 130.

In an aspect, each appendage 110 can be configured to have an articulation state 230. In an example, the articulation state 230 can be a rigidity of the appendage 110. In an example, the rigidity of the appendage 110 can be varied by modifying an amount of pressurized gas/fluid delivered to the appendage 110. In an example, the rigidity of the appendage 110 can be varied by modifying the viscosity of the gas/fluid delivered to the appendage 110.

In an example, the articulation state 230 can be a combination of the articulation shape 200 and the rigidity of the appendage 110. U.S. patent application Ser. No. 14/243,656 titled "Systems and methods for actuating soft robotic actuators" and international patent application WO2013148340A2 titled "Systems and methods for providing flexible robotic actuators" describe methods to control a state of a soft actuator and are both hereby incorporated by reference in their entirety.

Sensors

Figure 6A:
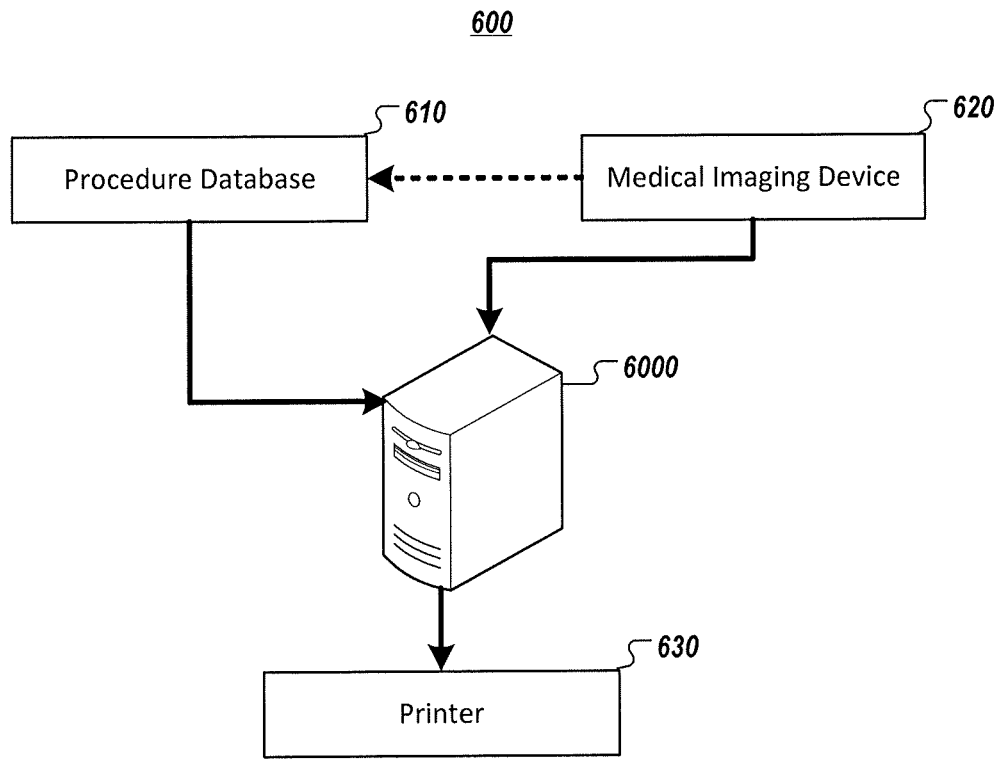
FIG. 6A shows a system for printing an appendage including a procedure database, a medical imaging device, a computing device, and a printer according to an example.
Figure 6B:
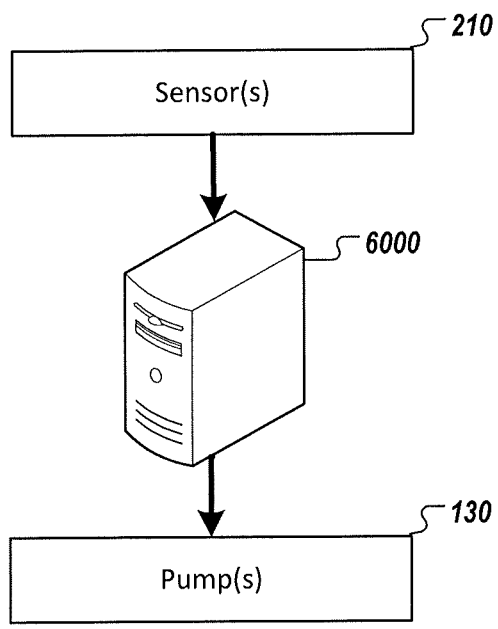
FIG. 6B shows a system configured for closed-loop control of the soft surgical tool according to an example.

In an example, each appendage 110 can include one or more sensors 210 configured to provide feedback such as for closed-loop control (See FIG. 6B). In an example, the one or more sensors 210 can be positioned along a length of each appendage 110. In an example, the one or more sensors 210 can be positioned around a width of each appendage 110. In an example, combined readings from two or more sensors 210 can be configured to provide a 3D orientation of each appendage 110 to ensure proper use of the soft surgical tool 100. The sensors 210 may be proximity sensors, infrared sensors, tactile switches, relays, force sensors, or other devices that can provide feedback of the surgical scene, and current state of the soft surgical tool 100.

In an example, the one or more sensors 210 can be configured to sense a contact pressure applied to the tissue. In an example, the soft surgical tool 100 is configured to modify at least one pump 130 based on a reading from at least one sensor 210 such that the contact pressure applied to the tissue is atraumatic. In an example, the one or more sensors 210 can be configured to sense a tissue property upon contact according to an example. Examples of tissue properties include optical properties such as color, patterns, and contour, mechanical properties such as stiffness, and physiological properties such as an amount of vascularity.

Appendage Segments

Figure 3A:
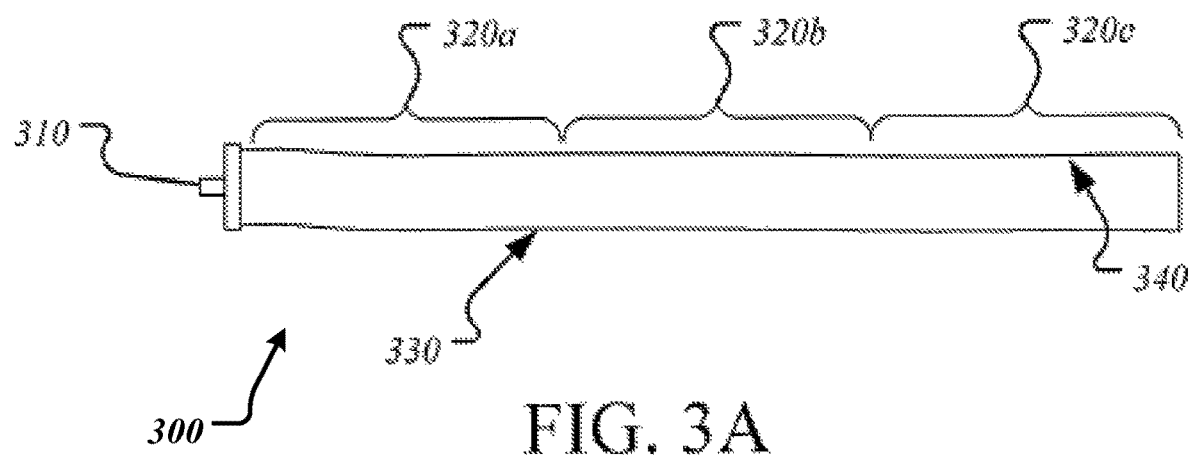
FIG. 3A is a drawing of an appendage divided into a set of segments, where each segment is configured to actuate in a different way according to an example.
Figure 3B:
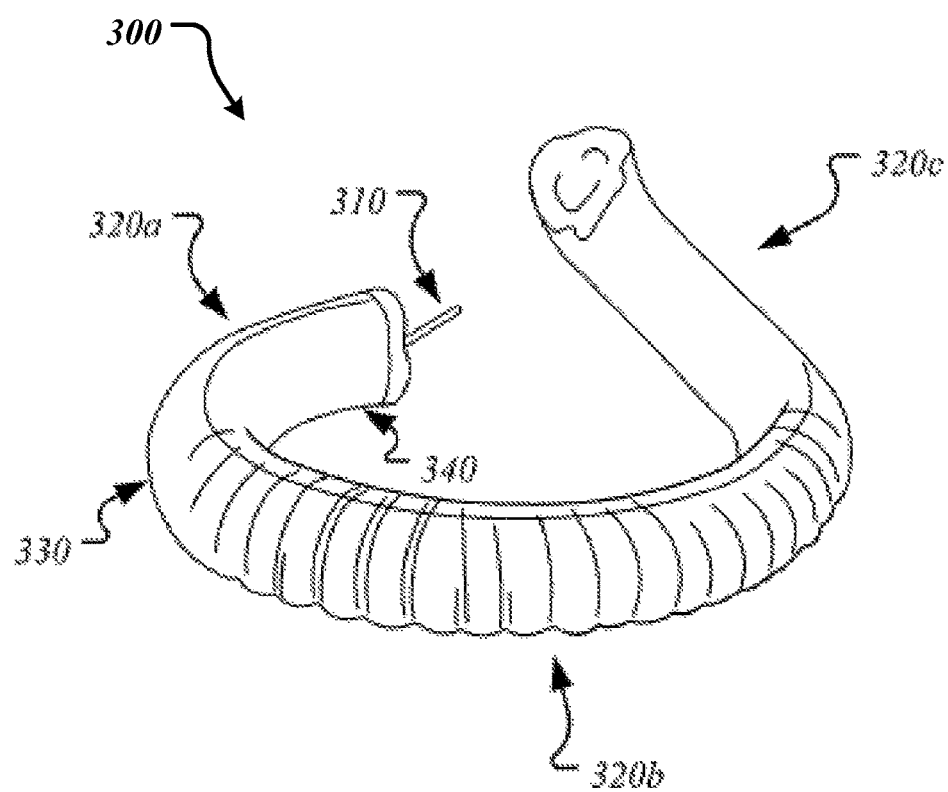
FIG. 3B is a perspective drawing of the appendage shown in FIG. 3A where each segment is actuated in a different way according to an example.

FIG. 3A is a drawing of an appendage 300 divided into a set of appendage segments 320a-c, where each appendage segment 320a-c is configured to actuate in a different way according to an example. With reference to the appendage 300 of FIG. 3B, the appendage segment 320a can be configured to bend, the appendage segment 320b can be configured to extend, and the appendage segment 320c can be configured to simultaneously bend and twist. In an example, each appendage 300, 110 can include one or more inlets 310 connected to a pump 130 configured to control a direction and an amount of flow 370 (See FIGS. 3D and 3F).

In an example, each appendage segment 320a-c can have a combination of an opposing compliant wall 330 and a rigid wall 340 which are mechanically biased to actuate in one or more directions. When a gas/fluid is pumped into the appendage 110, the compliant walls 330 expand while the rigid walls 340 maintain a predetermined length, such that the appendage 110 flexes in the direction of the rigid walls 340. In an aspect, two or more appendage segments 320 can form a joint and facilitate articulation of the appendage 110 into an articulation shape 200. In an example, the viscosity of the gas/fluid filling the two or more appendage segments 320 can be configured to modify the articulation state 230 of the appendage 110. U.S. patent application Ser. No. 14/329,506 titled "Flexible robotic actuators", U.S. patent application Ser. No. 13/885,967 titled "Soft robotic actuators", and E.U. patent application EP1319845A2 titled "Flexible actuator" describe soft robotic actuators that are composed of one or more flexible chambers with a rigid spine and are all hereby incorporated by reference in their entirety.

Figure 3C:
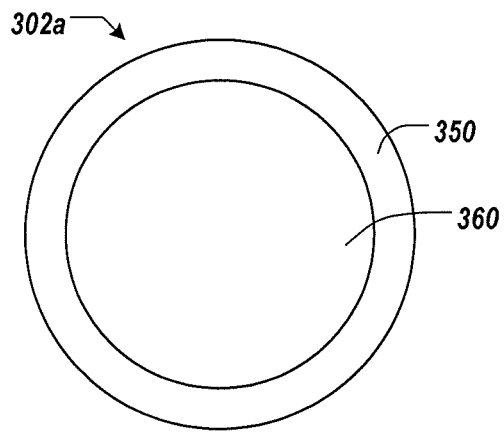
FIG. 3C shows a cross-section across an appendage width of an appendage including an outer membrane and an inner channel according to an example.
Figure 3D:
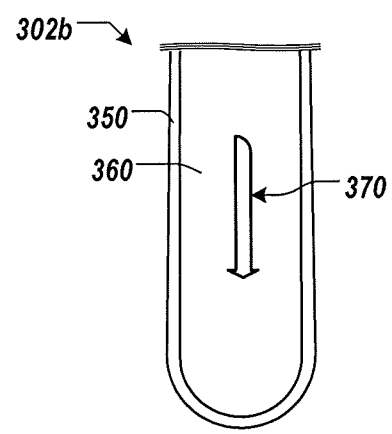
FIG. 3D shows a cross-section across an appendage length of the appendage shown in FIG. 3C showing a flow within the inner channel according to an example.

FIG. 3C shows a cross-section across an appendage width 302a of an appendage 302 including an outer membrane 350 and an inner channel 360 according to an example. FIG. 3D shows a cross-section across an appendage length 302b of the appendage 302 shown in FIG. 3C showing a flow 370 within the inner channel 360 according to an example. In an example, at least one pump 130 can be configured to pump a fluid/gas at a certain pressure to create the flow 370. In an aspect, the flow 370 is configured to actuate each appendage 110 into an articulation shape 200.

Figure 3E:
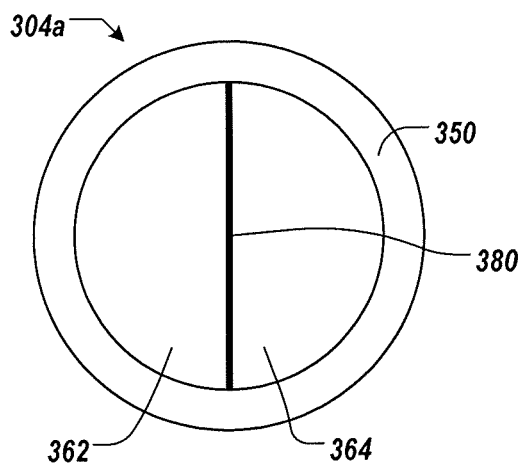
FIG. 3E shows a cross-section across an appendage width of an appendage including an outer membrane and a channel divider configured to partition the inner channel according to an example.
Figure 3F:
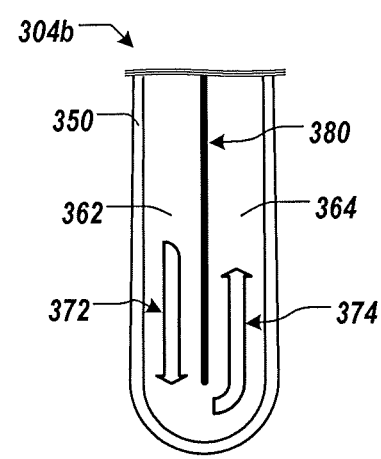
FIG. 3F shows a cross-section across an appendage length of the appendage shown in FIG. 3E showing two flow directions directed by the channel divider within the inner channel according to an example.

FIG. 3E shows a cross-section across an appendage width 304a of an appendage 304 including an outer membrane 350 and a channel divider 380 configured to partition an inner channel 360 into a first partition 362 and a second partition 364 according to an example. FIG. 3F shows a cross-section across an appendage length 304b of the appendage 304 shown in FIG. 3E. As shown in FIG. 3F, the channel divider 380 is configured to create a distal flow 372 within the first partition 362, where the distal flow 372 returns as a proximal flow 374 within the second partition 364 according to an example.

In an example, at least one pump 130 can be configured to pump a first fluid/gas having a first viscosity at a first pressure to create the distal flow 372. In an example, at least one pump 130 can be configured to pump a second fluid/gas having a second viscosity at the same or another pressure to create the distal flow 372. In an example, at least one pump 130 can be configured to interchange the first fluid/gas and the second fluid/gas in order to modify a stiffness or rigidity of the appendage in at least one of the appendage width or the appendage length direction. In an example, the appendage 110 having higher viscosity gas/fluid can apply more force when used in a surgical application such as grasping. In an example, each pump 130 may have different reservoirs 140 when a specific gas/fluid is used to inflate each appendage 110. Viscosity for example could be modified based on temperature, for example, by including a heating element in the line.

Hybrid Appendage

Figure 4A:
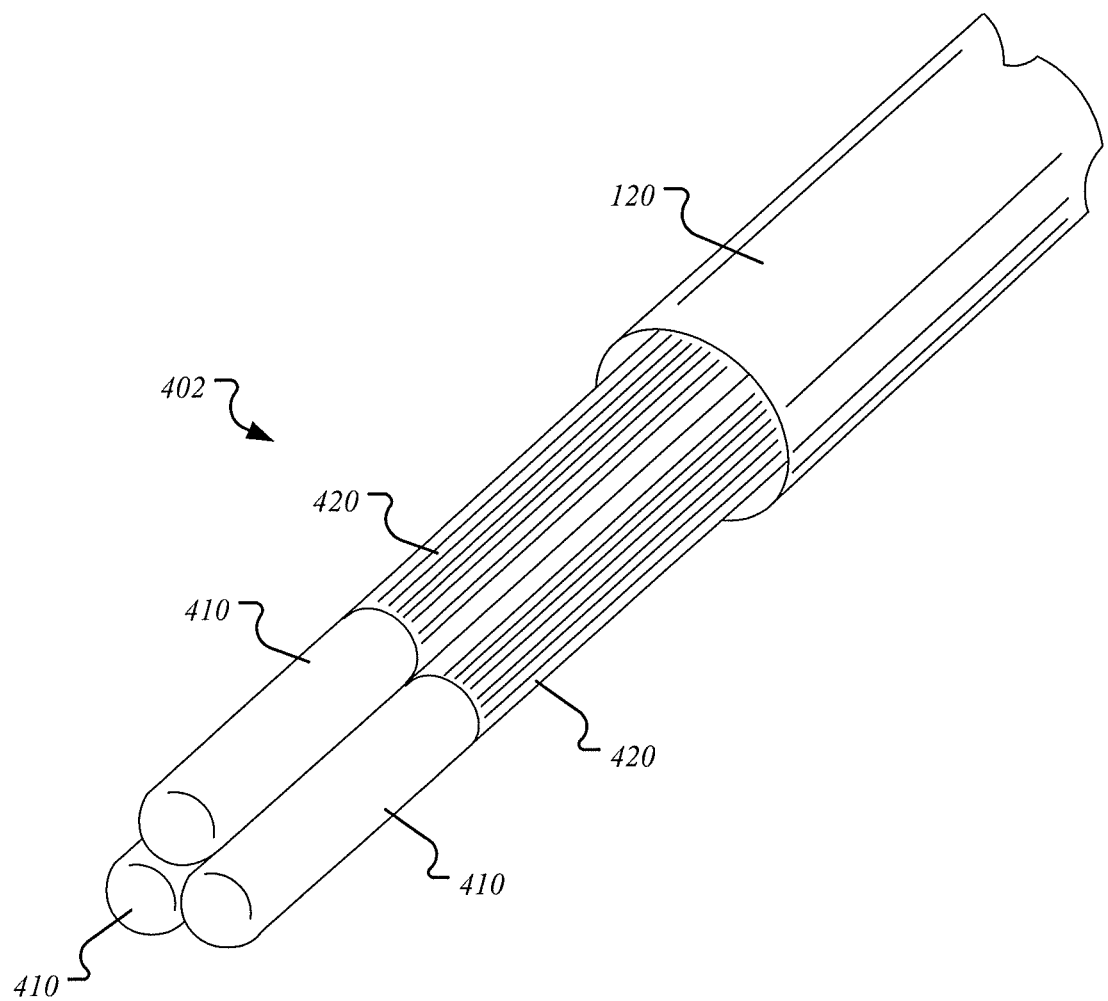
FIG. 4A is a perspective drawing of close up of a distal tip of the soft surgical tool illustrating a hybrid appendage having a compliant portion and a rigid portion according to an example.

FIG. 4A is a perspective drawing of close up of a distal tip of a soft surgical tool 100 including a set of hybrid appendages 402 where each hybrid appendage 402 has a compliant portion 410 and a rigid portion 420 according to an example. The compliant portion 410 is preferably at the distal tip; however there can be a second rigid portion extending further distally according to an example. In an example, the compliant portion 410 and the rigid portion 420 can be based on a variation of a number of windings of the shape-memory material around an appendage segment 320.

Orienting Assembly

Figure 4B:
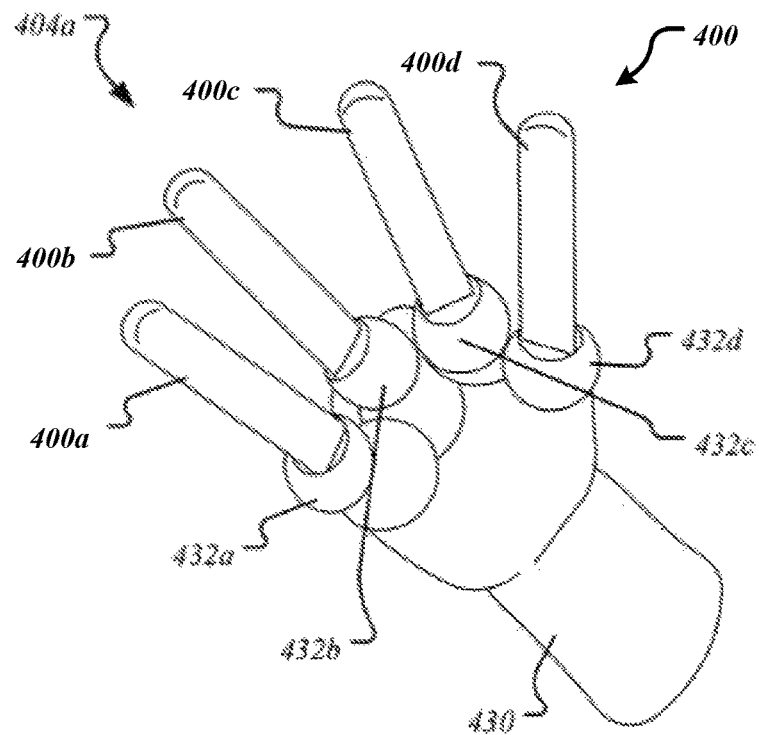
FIGS. 4B-4C show perspective drawings of close up of a distal tip of a soft surgical tool including an orienting assembly having a plurality of apertures, where each aperture is configured to orient an appendage according to an example.
Figure 4C:
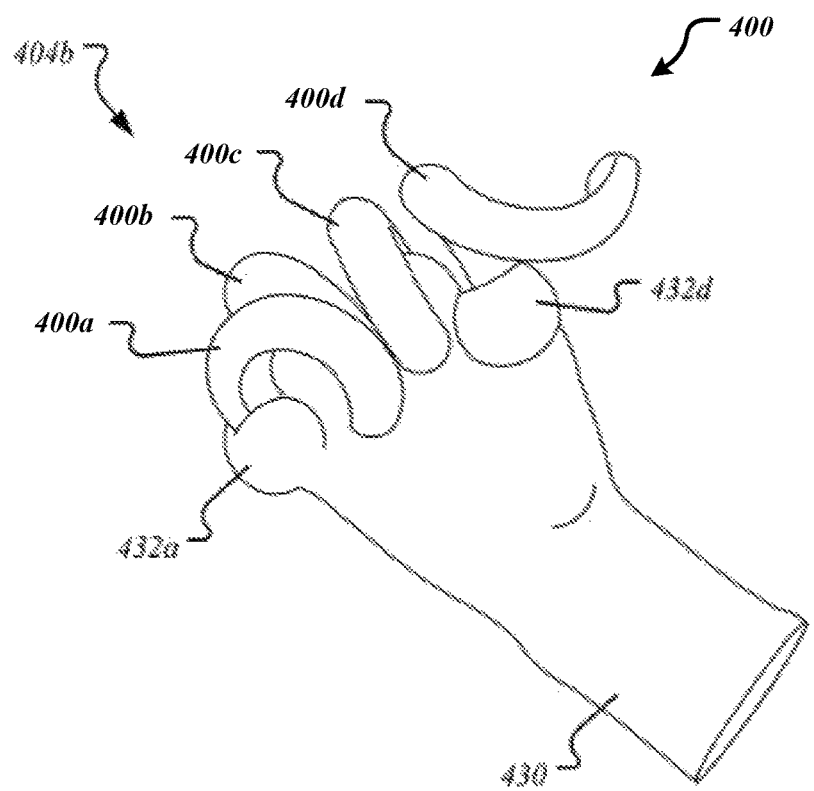

FIGS. 4B-4C show perspective drawings of close up of a distal tip of a soft surgical tool 100 including an orienting assembly 430 having a set of apertures 432a-d, where each aperture 432a-d is configured to orient an appendage 400a-d of a set of appendages 400 relative to the orienting assembly 430 according to an example. In an example, the set of apertures 432a-d can be configured to orient the set of appendages 400 to resemble one or more thumbs and one or more fingers. In an example, the set of appendages 400 can be actuated in a first articulation state 230' such that the orienting assembly 430 has a first assembly 404a (See FIG. 4B). Further, the set of appendages 400 can be actuated in a second articulation state 230' such that the orienting assembly 430 has a second assembly 404b (See FIG. 4C). In an example, each assembly 404a-b can be configured for a particular function such as a grasping motion to hold a portion of tissue and a retraction of tissue to open the surgical field. U.S. patent application Ser. No. 14/464,396 titled "Low strain pneumatic networks for soft robots" and U.S. patent application Ser. No. 14/421,429 titled "Apparatus, systems, and methods for modular soft robots" describe how multiple actuators can be synchronized to create a soft robotic system and are both hereby incorporated by reference in their entirety. U.S. patent application Ser. No. 14/114,833 titled "Robot having soft arms for locomotion and grip purposes", describes a robotic system that uses soft actuators as a fingered grasper to pick and place objects and is hereby incorporated by reference in its entirety.

Patient-Specific Appendage

In an aspect, an appendage 110 can be a patient-specific appendage. In an example, the patient-specific appendage can be based on preoperative imaging (e.g., MRI, CT, ultrasound, etc.) of a patient. The patient can be preoperatively imaged/scanned by a medical imaging device 620 (See FIG. 6A) to determine a location and geometry of anatomical structures inside the abdominal cavity. For example, at least one of a size, a shape, and orientation of the anatomical structure, target tissue, and organ can be determined based on preoperative imaging and used to generate the patient-specific appendage. In the case of appendectomy, multispectral imaging can be used to identify an inflamed appendix.

In an example, the preoperative imaging of the patient can be configured to provide a set of geometric constraints and a set of motion paths that are unique to the patient. In an example, a computing device 6000 (see below) can be configured to generate a patient-specific actuation program that is generated based on the preoperative imaging or by a predetermined library of actuation commands based on the surgical procedure.

The patient-specific appendage can be generated having a combination of the rigid walls 340 and compliant walls 330 configured to match the mechanical constraints of the set of geometric constraints and the set of motion paths. In an example, the patient-specific appendage can be generated using 3D printer configured to print with biocompatible materials.

Procedure-Specific Appendage

In an aspect, an appendage 110 can be a procedure-specific appendage based on one or more procedure steps of a surgical procedure. In an example, the procedure-specific appendage can have a predetermined motion and a set of articulation states 230 that are configured to form the predetermined motion. In an embodiment, the soft surgical tool 100 can have preprogrammed articulations that are based on a geometry and material used of the set of appendages 120.

In an alternative embodiment, the soft surgical tool 100 can include a quick connect feature that allows quick removal of any appendage 120 and connection of the procedure-specific appendage such that the procedure-specific appendage designed for specific surgeries or parts of surgery can be quickly replaced on a same mechanical interface of the soft surgical tool 100 in order to carry out a surgical task or procedure. The appendages could also be of different sizes, shapes or functions for varied placement or use.

Figure 5A:
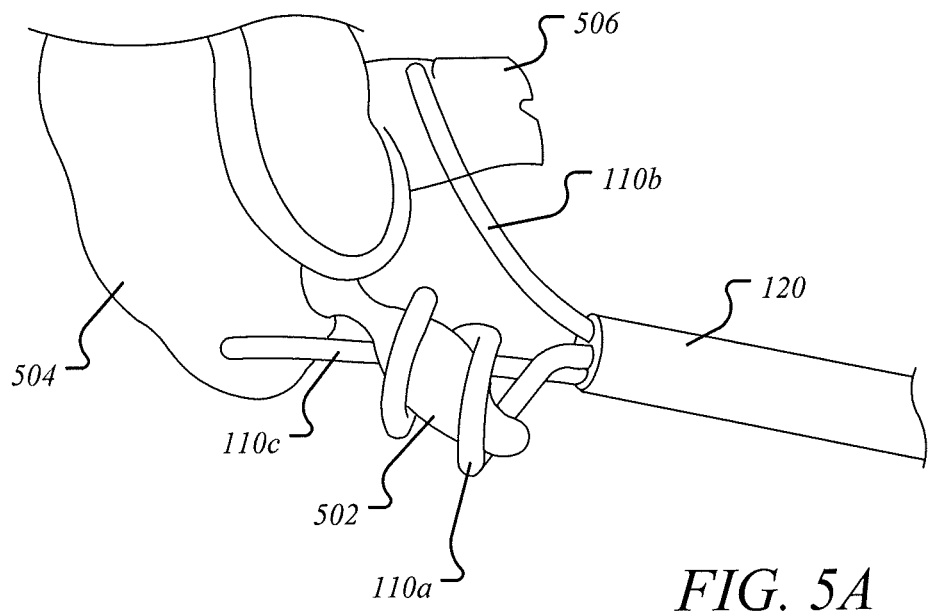
FIGS. 5A-5B show a frontal view and lateral view respectively of the soft surgical tool being used to stabilize an appendix in an appendectomy procedure according to an example.
Figure 5B:
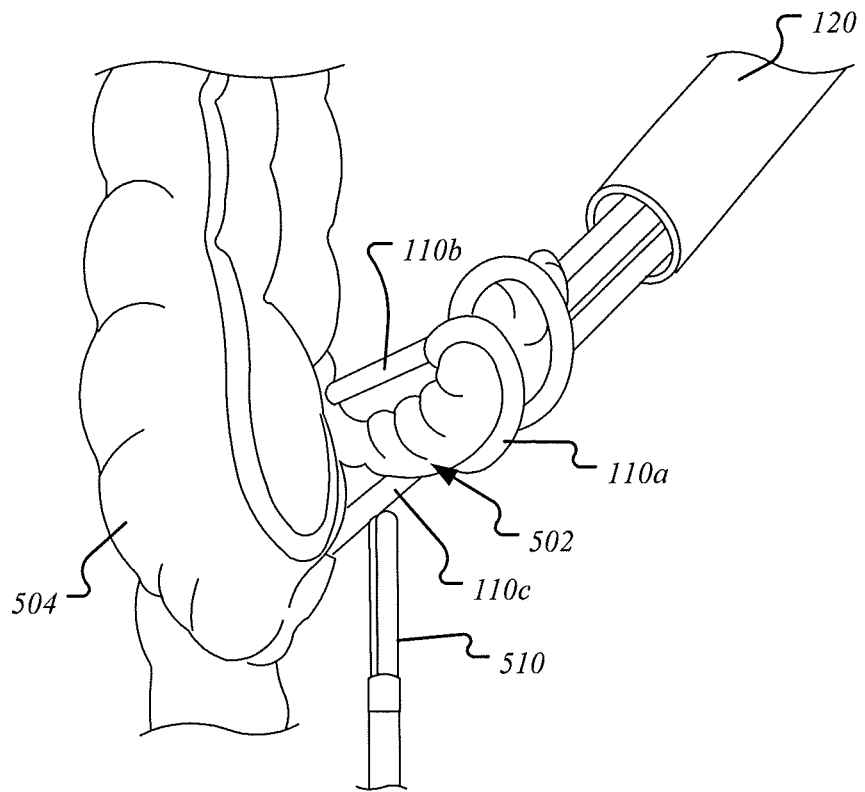

FIGS. 5A-5B show a frontal view and lateral view respectively of the soft surgical tool 100 being used to stabilize an appendix 502 attached to a cecum 504 of a body in an appendectomy procedure according to an example. As best shown in FIG. 5A, the appendages 110b-110c each are actuated into a curved shape and are configured to retract portions of the cecum 504 and the terminal ilium 506 respectively of a patient surrounding the appendix 502. The appendage 110a is shown circulating and stabilizing the appendix 502. In an example, the appendage 110a configured to circulate and to stabilize the appendix 502 can be considered a procedure-specific appendage. FIG. 5B shows the soft surgical tool 100 positioning the appendix 502 away from the cecum 504 and introducing a laparoscopic stapler 510, which is used to cut the appendix 502.

System for Printing an Appendage

FIG. 6A shows a system for printing an appendage including a procedure database 610, a medical imaging device 620, a computing device 6000, and a printer 630 according to an example. In an example, the printer 630 can be a 3D printer such as the M1 from Carbon3D, Inc. (Redwood City, Calif.). In an example, the computing device 6000 is configured to receive a set of mechanical constraints for a surgical procedure from at least one of the procedure database 610 and the medical imaging device 620. In an example, the procedure database 610 can be used to store the set of mechanical constraints for a surgical procedure from the medical imaging device 620.

In an example, the computing device 6000 is configured to calculate a set of articulation states based on the set of mechanical constraints. In an example, the computing device 6000 is configured to generate a plurality of print commands for printing an appendage configured to form the set of articulation states based on the calculation of the set of articulation states. In an example, a print command can include modifying a thickness of a wall of the appendage 110. For example, a procedure specific appendage can be modified into a patient-specific appendage by either adding or removing material from a wall of the appendage 110.

In an example, the printer 630 is configured to receive the plurality of print commands from the computing device 6000 and to print the appendage 110 based on the plurality of print commands.

Closed-Loop Control

FIG. 6B shows a system 600 for providing closed-loop control of the soft surgical tool 100 according to an example. In an example, the closed-loop control of the soft surgical tool 100 can be done by taking readings from the one or more sensors 210, making a comparison of the readings by the computing device 6000, and controlling the set of pumps 130 to modify an internal pressure of an appendage 110 based on the comparison. Automatic positioning of the soft surgical tool 100 can be accomplished through a motion tracking algorithm targeting optical markers on the tissue according to an example. The set of pumps 130 can automatically and independently inflate each appendage based on an algorithm configured to track a present the step of the surgical procedure, and update the soft surgical tool 100 for a next step of the surgical procedure.

In an example, positioning and operation of the soft surgical tool 100 is accomplished with a master-slave paradigm where the actuation state of the soft surgical tool 100 is controlled by the surgeon. In an example, the sensor feedback can be used in a control algorithm to automatically complete a surgical task.

Figure 6C:
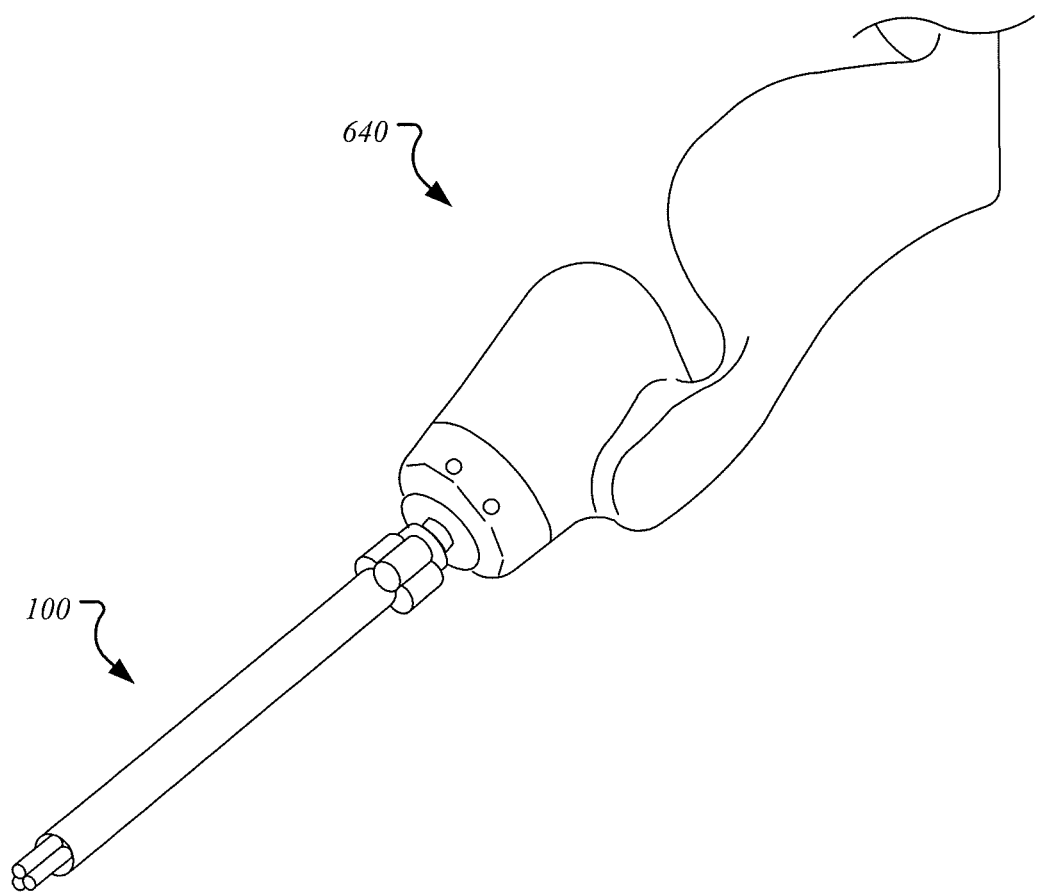
FIG. 6C shows the soft surgical tool mounted to a robotic positioning platform for use in a robotic surgical procedure according to an example.

In an example, as shown in FIG. 6C, the soft surgical tool 100 can be mounted to a robotic positioning platform 640 for use in a robotic surgical procedure. In an example, the soft surgical tool 100 can be incorporated in a robotic system such as the surgical tool described in U.S. Pat. No. 9,220,570 titled "Automated surgical and interventional procedures" which is hereby incorporated by reference in its entirety. In an example, the soft surgical tool 100 can be incorporated in a robotic system such as the da Vinci® Surgical System from Intuitive Surgical, Inc. (Sunnyvale, Calif.). In another example, the soft surgical tool 100 can be incorporated in a robotic hand tool such as the Kymerax® from Terumo Medical Corporation (Somerset, N.J.).

Hardware Description of Computing System

Figure 6D:
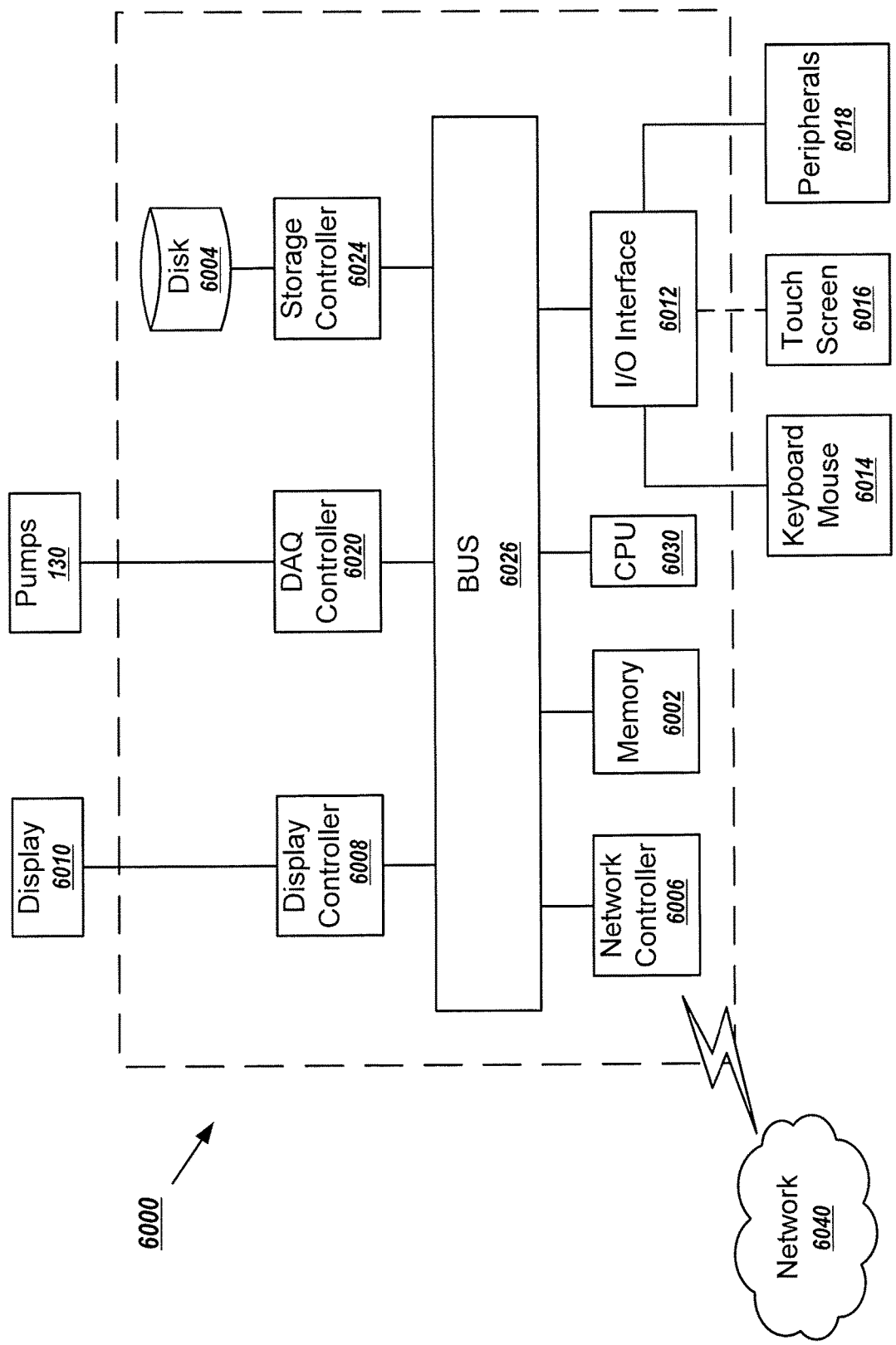
FIG. 6D shows hardware of the computing device according to an example.

Next, a hardware description of a computing device 6000 according to exemplary embodiments is described with reference to FIG. 6D. In FIG. 6D, the computing device 6000 or server includes a CPU 6030 which performs the processes described above. The process data and instructions may be stored in memory 6002. These processes and instructions may also be stored on a storage medium disk 6004 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device or server communicates, such as another server, computer or database.

Further, a portion of the claimed advancements may be provided as a utility application, background daemon, or component of an operating system, or combination thereof, executing in conjunction with CPU 6030 and an operating system such as Microsoft Windows® 7, UNIX®, Solaris®, LINUX®, Apple®, macOS® and other systems known to those skilled in the art.

CPU 6030 may be a Xenon or Core processor from Intel of America or an Opteron processor from AMD of America, or may be other processor types that would be recognized by one of ordinary skill in the art. Alternatively, the CPU 6030 may be implemented on an FPGA, ASIC, PLD or using discrete logic circuits, as one of ordinary skill in the art would recognize. Further, CPU 6030 may be implemented as multiple processors cooperatively working in parallel to perform the instructions of the inventive processes described above.

The computing device or server in FIG. 6D also includes a network controller 6006, such as an Intel Ethernet PRO network interface card from Intel Corporation of America, for interfacing with network 6040. As can be appreciated, the network 6040 can be a public network, such as the Internet, or a private network such as an LAN or WAN network, or any combination thereof and can also include PSTN or ISDN sub-networks. The network 6040 can also be wired, such as an Ethernet network, or can be wireless such as a cellular network including EDGE, 3G and 4G wireless cellular systems. The wireless network can also be WiFi, Bluetooth®, or any other wireless form of communication that is known. In an example, the network 6040 can be configured to access a database storing a plurality of mechanical constraints based on the surgical procedure.

The computing device or server further includes a display controller 6008, such as a NVIDIA® GeForce® GTX or Quadro graphics adaptor from NVIDIA® Corporation of America for interfacing with display 6010, such as a Hewlett Packard HPL2445w LCD monitor. A general purpose I/O interface 6012 interfaces with a keyboard and/or mouse 6014 as well as a touch screen panel 6016 on or separate from display 6010. General purpose I/O interface also connects to a variety of peripherals 6018 including printers and scanners, such as an OfficeJet or DeskJet from Hewlett Packard.

A data acquisition (DAQ) controller 6020 is also provided in the computing device or server, to interface with the set of sensors 210 and the set of pumps 130 thereby providing closed-loop control.

The general purpose storage controller 6024 connects the storage medium disk 6004 with communication bus 6026, which may be an ISA, EISA, VESA, PCI, or similar, for interconnecting all of the components of the computing device or server. In an example, the storage medium disk 6004 can act as a database storing a plurality of mechanical constraints based on the surgical procedure. A description of the general features and functionality of the display 6010, keyboard and/or mouse 6014, as well as the display controller 6008, storage controller 6024, network controller 6006, DAQ controller 6020, and general purpose I/O interface 6012 is omitted herein for brevity as these features are known.

One or more processors can be utilized to implement various functions and/or algorithms described herein, unless explicitly stated otherwise. Additionally, any functions and/or algorithms described herein, unless explicitly stated otherwise, can be performed upon one or more virtual processors, for example on one or more physical computing systems such as a computer farm or a cloud drive.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks. Moreover, the present disclosure is not limited to the specific circuit elements described herein, nor is the present disclosure limited to the specific sizing and classification of these elements.

Method for Assembling a Soft Surgical Tool

Figure 7B:
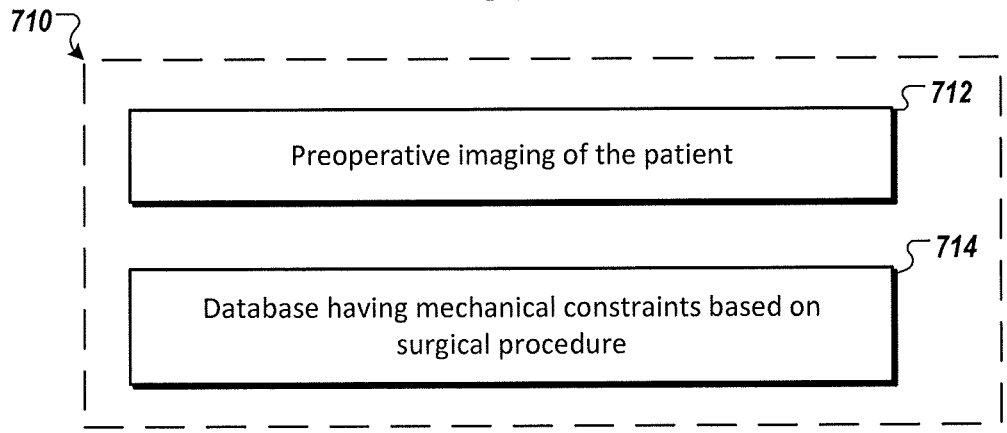
FIG. 7B shows different examples for receiving a set of mechanical constraints for a surgical procedure.
Figure 7C:
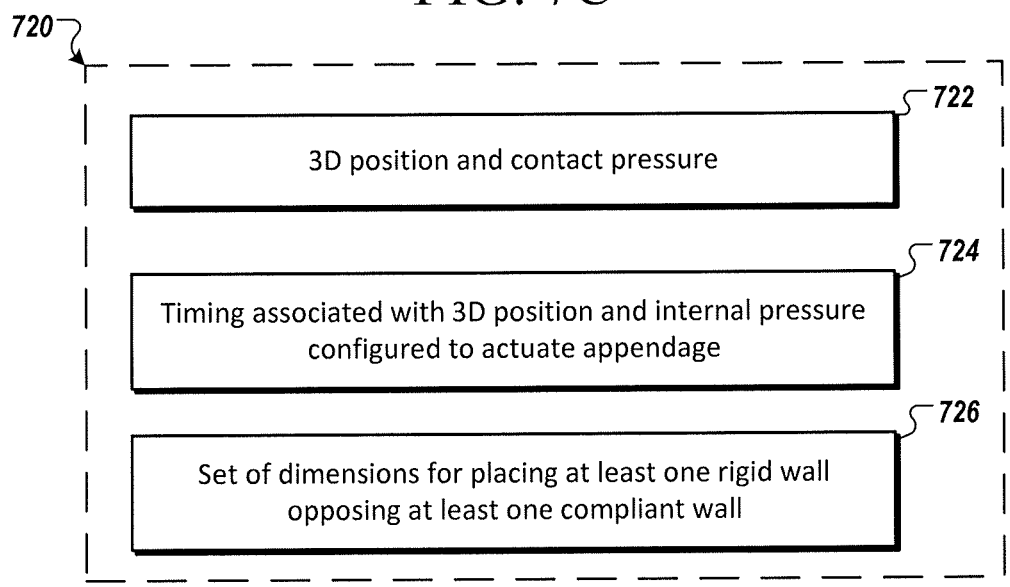
FIG. 7C shows different examples for calculating a set of articulation states.
Figure 7D:
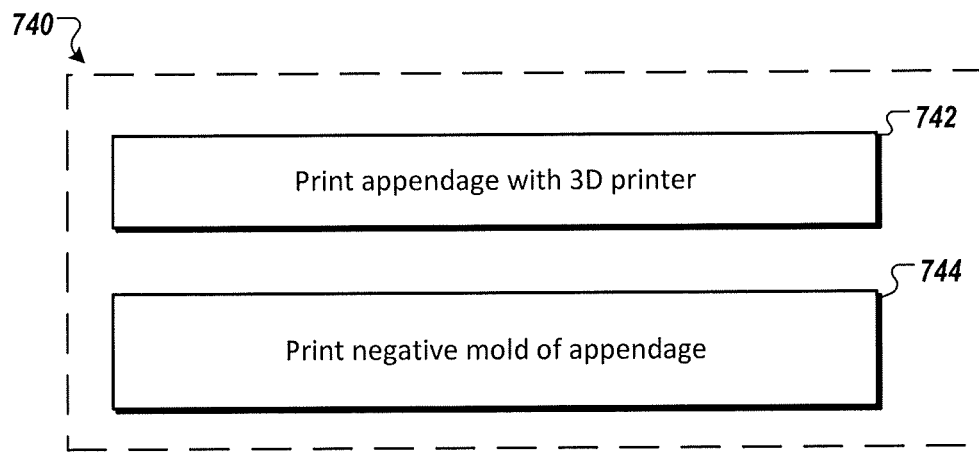
FIG. 7D shows different examples for printing an appendage.

FIG. 7A is a flowchart showing a method 700 for making a soft surgical tool 100 according to an example. The method 700 includes a step 710 of receiving a set of mechanical constraints for a surgical procedure. In an example, the set of mechanical constraints can be received from preoperative imaging of the patient (712). In an example, the set of mechanical constraints can be received from a database storing a plurality of mechanical constraints based on the surgical procedure (714). In an example, the set of mechanical constraints can be based on the location and geometry of anatomical structures inside the abdominal cavity of the patient. In an example, the set of mechanical constraints can be based on a surgical field needed to perform the surgical procedure. In an example, the set of mechanical constraints can include a timing corresponding to each mechanical constraint.

At step 720, calculate a set of articulation states based on the set of mechanical constraints. In an example, the calculation of an articulation state can include a 3D position and a contact pressure (722). In an example, the contact pressure is based on a pressure threshold that is atraumatic to the tissue. In an example, the calculation of an articulation state can further include a timing associated with the 3D position and an internal pressure configured to actuate the appendage (724). In an example, the calculation of an articulation state can include calculating a set of dimensions for placing at least one rigid wall opposing at least one compliant wall (726).

At step 730, generate a plurality of print commands for printing an appendage configured to form the set of articulation states based on the calculation of the set of articulation states. In an example, the plurality of print commands are based on features available using the printer. In an example, the printer can be a 4D printer where the materials used in 3D printing are configured to change shape after printing.

In an example, the method 700 may further include a step 740, where an appendage is printed based on the plurality of print commands. In an example, the appendage can be printed directly using the 3D printer (742). In an example, the printing of the appendage includes printing an appendage mold having a negative shape of the appendage (744). The appendage mold can be used with traditional molding methods in order to finalize fabrication of the appendage.

In an example, the method 700 may further include a step 750, where two or more printed appendages are assembled into an orienting assembly 430. Further, other subsystems such as wiring for the sensors can be assembled according to an example.

Appendectomy Procedure Using a Soft Surgical Tool

Next, a description is provided of a workflow of how the soft surgical tool 100 can be used to assist in an appendectomy procedure as illustrated in FIGS. 5A-5B according to an example. Optionally, a patient can be preoperatively imaged to determine a location and geometry of all their important structures inside their abdominal cavity. A set of articulation states can be determined based on the locations and geometry of all the patient's important structures. In an example, the soft surgical tool 100 can have a set of appendages held within the sheath that can be mechanically programed to follow a unique or abnormal geometry within the patient.

The soft surgical tool 100 can be inserted inside the abdominal cavity and the sheath 120 can be retracted to expose the set of appendages. Each appendage can be actuated into a first actuation state. In an example, an appendage can be actuated into the first actuation state by using at least one pump to inflate the appendage to a first internal pressure. An omentum covering the appendix 502 can be brushed aside with a swiping motion of the soft surgical tool 100, exposing underlying tissue.

Next, the set of appendages can be positioned above the appendix 502. A first appendage can be actuated to a second actuation state configured to push the cecum 504 down. A second appendage can be actuated to a second actuation state configured to push the terminal ilium 506 down. A third appendage can be actuated to a second actuation state configured to create a spiraling motion that helically wraps around a base of the appendix 502 and stabilize the appendix 502 as illustrated in FIGS. 5A-5B. Taken together, the set of appendages form an orienting assembly 430 configured to act as a retractor tool, opening the surgical field.

Once the appendix 502 is immobilized, a laparoscopic stapler can be brought into the surgical field, and used to separate the appendix 502 from the cecum 504. After the appendix 502 is separated from the cecum 504, the orienting assembly 430 can be retracted such that the appendix 502 is dropped in a bag (not shown), and the cecum 504 and terminal ilium 506 are no longer retracted. The sheath 120 can be advanced back over the set of appendages and the soft surgical tool can be retracted from the patient.

Alternative Embodiments

In an alternative embodiment, one or more of the appendages can include a feature to cut, dissect, or biopsy tissue (not shown). Articulation of the appendage can cause the soft surgical tool 100 to cut in a preformed pattern or a pattern generated from preoperative imaging. In an alternative embodiment, one or more of the appendages can include a traditional tool for tissue manipulation such as a grasper to push, pull, pick up, and retract tissue, tools, and cameras in the surgical field.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A soft surgical tool for use in a surgical procedure, comprising:
   at least one reservoir configured to hold a fluid having a corresponding viscosity;
   at least one appendage having a plurality of appendage segments forming an articulation shape, the at least one appendage having a length and an internal channel that is continuous through the plurality of appendage segments and substantially cylindrical along the length of the at least one appendage; and
   at least one pump configured to
     pressurize the fluid held within the at least one reservoir, and
     provide the pressurized fluid to the internal channel of the at least one appendage,
   wherein each of the plurality of appendage segments has at least one compliant wall configured such that, when the at least one appendage is inflated by the pressurized fluid provided to the internal channel, the least one compliant wall actuates the at least one appendage based on the corresponding viscosity of the pressurized fluid.

2. The soft surgical tool of claim 1, further comprising a sheath configured to house the at least one appendage.

3. The soft surgical tool of claim 1, wherein the at least one appendage further comprises
   a sensor configured to sense a contact pressure of the at least one appendage with respect to a tissue of a patient.

4. The soft surgical tool of claim 1, wherein the articulation shape is based on a preoperative image of a patient.

5. The soft surgical tool of claim 1, wherein a selection of the at least one appendage is based on a preoperative image of a patient.

6. The soft surgical tool of claim 1, further comprising processing circuitry configured to
   control the at least one pump to pressurize the fluid and to provide the pressurized fluid to the internal channel in order to actuate the at least one appendage.

7. The soft surgical tool of claim 6, wherein the processing circuitry is configured to
   control the at least one pump to actuate the at least one appendage based on a preoperative image of a patient.

8. The soft surgical tool of claim 1, wherein the fluid is an inert gas.

9. The soft surgical tool of claim 1, wherein the at least one reservoir is further configured to hold a second fluid having a different viscosity, and the at least one pump is configured to cycle the fluid and the second fluid.

10. The soft surgical tool of claim 9, wherein the at least one appendage is configured to actuate with a varying force.

11. The soft surgical tool of claim 9, wherein the at least one appendage is configured to actuate into a different articulation shape.

12. The soft surgical tool of claim 1, wherein the internal channel of the at least one appendage includes a channel divider that extends, from a proximal end of the at least one appendage, along a longitudinal axis of the at least one appendage and forms a first partition of the internal channel and a second partition of the internal channel, the first partition and the second partition being in fluid communication at a distal end of the at least one appendage.

* * * * *